United States Patent [19]

Johnson

[11] 4,235,783
[45] Nov. 25, 1980

[54] TRANS-2,3,4,5-TETRADEHYDRO-9-DEOXY-5,9A-EPOXY-PGF$_1$ AMIDES

[75] Inventor: Roy A. Johnson, Kalamazoo, Mich.

[73] Assignee: The Upjohn Company, Kalamazoo, Mich.

[21] Appl. No.: 73,463

[22] Filed: Sep. 7, 1979

Related U.S. Application Data

[60] Division of Ser. No. 936,295, Aug. 23, 1978, which is a division of Ser. No. 819,856, Jul. 28, 1977, Pat. No. 4,123,441, which is a continuation-in-part of Ser. No. 725,546, Sep. 22, 1976, abandoned, which is a continuation-in-part of Ser. No. 716,960, Aug. 23, 1976, abandoned.

[51] Int. Cl.$^3$ ............................................ C07D 311/02
[52] U.S. Cl. ................................. 260/345.2; 542/420; 542/421; 542/426; 542/429
[58] Field of Search ...................... 260/345.2; 542/421, 542/426, 429, 420

[56] References Cited

PUBLICATIONS

Pace-Asciak et. al., Biochem., 10, 3657 (1971).
Pace-Asciak et. al., Jacs, 98, 2348 (1976).

*Primary Examiner*—Nicky Chan
*Attorney, Agent, or Firm*—Robert A. Armitage

[57] ABSTRACT

The present invention relates to novel trans-2,3,4,5-tetradehydro-9-deoxy-5,9a-epoxy-PGF$_1$ amides, which are useful for inducing a variety of prostacyclin-like pharmacological effects. Accordingly, these compounds are useful pharmacological agents for the same purposes for which prostacyclin is employed.

8 Claims, No Drawings

TRANS-2,3,4,5-TETRADEHYDRO-9-DEOXY-5,9A-EPOXY-PGF$_1$ AMIDES

DESCRIPTION

CROSS REFERENCE TO RELATED APPLICATION

The present application is a divisional application of U.S. Ser. No. 936,295, filed Aug. 23, 1978, now pending issuance as a U.S. patent; which is a divisional application of U.S. Ser. No. 819,856, filed July 28, 1977, now U.S. Pat. No. 4,123,441; which is a continuation-in-part application of U.S. Ser. No. 725,546, filed Sept. 22, 1976, now abandoned; which is a continuation-in-part application of U.S. Ser. No. 716,960, filed Aug. 23, 1976, now abandoned.

BACKGROUND OF THE INVENTION

The present invention relates to novel trans-2,3,4,5-tetradehydro-9-deoxy-5,9α-epoxy-PGF$_1$ amides, which are useful for inducing a variety of prostacyclin-like pharmacological effects. Accordingly, these compounds are useful pharmacological agents for the same purposes for which prostacyclin is employed.

The essential material constituting a disclosure of the preparation and use of the novel compounds of the present invention is incorporated here by reference from U.S. Pat. No. 4,123,441.

SUMMARY OF THE INVENTION

The present invention particularly provides:
a 4Z compound of the formula

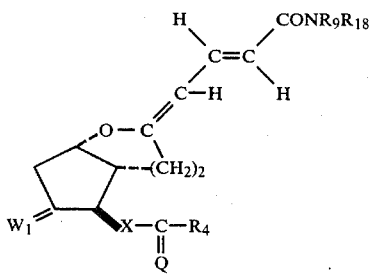

wherein
W$_1$ is a α—OH:β—H, α—H:β—OH, oxo, methylene, α—H:β—H, α—CH$_2$OH:β—H;
wherein Q is oxo, α—H:β—H, α—OH:β—R$_8$ or α—R$_8$:β—OH
wherein R$_8$ is hydrogen or alkyl of one to 4 carbon atoms, inclusive; and
wherein
R$_4$ is
(1) —CR$_5$R$_6$—C$_g$H$_{2g}$=CH$_3$
(2) —CR$_5$R$_6$—Z—(Ph)
(3) cis—CH$_2$—CH=CH—CH$_2$CH$_3$
wherein
C$_g$H$_{2g}$ is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro and the further proviso that neither R$_5$ nor R$_6$ is fluoro when Z is oxa (—O—);
wherein Z represents an oxa atom (—O—) or C$_j$H$_{2j}$
wherein C$_j$H$_{2j}$ is a valence bond or alkylene of one to 9 carbon atoms, inclusive, with one to 6 carbon atoms, inclusive between CR$_5$R$_6$— and the (Ph); wherein (Ph) is phenyl or phenyl substituted by one, 2, or 3 alkyl of one to 4 carbon atoms, inclusive, fluoro, chloro, trifluoromethyl, or —OR$_7$, wherein R$_7$ is alkyl of one to 4 carbon atoms, inclusive, with the proviso that not more than two such substituents are other than alkyl, such substituents being either the same or different;
wherein
R$_9$ is hydrogen, methyl, or ethyl, and wherein R$_{18}$ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive; and
wherein
X is
(1) trans—CH=CH—,
(2) cis—CH=CH—,
(3) —C≡C—, or
(4) —CH$_2$CH$_2$—; including the lower alkanoates thereof; and
a 4E compound of the formula

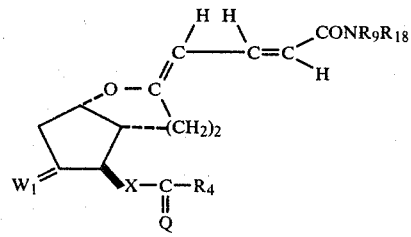

wherein
W$_1$ is α—OH:β—H, α—H:β—OH, oxo, methylene, α—H:β—H, α—CH$_2$OH:β—H;
wherein
Q is oxo, α—H:β—H, α—OH:β—R$_8$ or α—R$_8$:β—OH
wherein
R$_8$ is hydrogen or alkyl or one to 4 carbon atoms, inclusive; and
wherein
R$_4$ is
(1) —CR$_5$R$_6$—C$_g$H$_{2g}$—CH$_3$
(2) —CR$_5$R$_6$—Z—(Ph)
(3) cis—CH$_2$—CH=CH—CH$_2$CH$_3$
wherein
C$_g$H$_{2g}$ is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro and the further proviso that neither R$_5$ nor R$_6$ is fluoro when Z is oxa (—O—);
wherein Z represents an oxa atom (—O—) or C$_j$H$_{2j}$
wherein C$_j$H$_{2j}$ is a valence bond or alkylene of one to 9 carbon atoms, inclusive, with one to 6 carbon atoms, inclusive between CR$_5$R$_6$— and the (Ph); wherein (Ph) is phenyl or phenyl substituted by one, 2, or 3 alkyl of one to 4 carbon atoms, inclusive, fluoro, chloro, trifluoromethyl, or —OR$_7$, wherein R$_7$ is alkyl of one to 4 carbon atoms, inclusive, with the proviso that not more than two such substituents are other than alkyl, such substituents being either the same or different;
wherein $R_9$ is hydrogen, methyl, or ethyl, and wherein $R_{18}$ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive; and
wherein
X is
(1) trans—CH=CH—,
(2) cis—CH=CH—,
(3) —C≡C—, or
(4) —CH$_2$CH$_2$—;
including the lower alkanoates thereof.

With regard to the divalent substituents described in the claims, e.g., Q and $W_1$, these divalent radicals are defined as $\alpha$—$R_i$:$\beta$—$R_j$, where $R_i$ represents a substituent of the divalent moiety of the alpha configuration with respect to the cyclopentane and $R_j$ represents a substituent of the divalent moiety of the beta configuration with respect to the cyclopentane ring. Accordingly, when Q is defined as $\alpha$—OH:$\beta$—$R_8$, the hydroxy of the Q moiety is in the alpha configuration, i.e., as in prostacyclin, and the $R_8$ substituent is in the beta configuration. Not all carbon atoms to which such divalent moieties are attached represent asymmetric centers. For example, when both valence bonds are to hydrogen (e.g., $W_1$ or Q is $\alpha$—H:$\beta$—H), then no asymmetric center is present.

DESCRIPTION OF THE PREFERRED EMBODIMENTS

The present invention particularly relates to the following chemical compounds:
(4Z)-9-deoxy-5,9$\alpha$-epoxy-$\Delta$4-trans-$\Delta$2-PGF$_1$, amide;
(4Z)-9-deoxy-5,9$\alpha$-epoxy-$\Delta$4-trans-$\Delta$2-(15S)-15-methyl-PGF$_1$, amide;
(4Z)-9-deoxy-5,9$\alpha$-epoxy-$\Delta$4-trans-$\Delta$2-16,16-dimethyl-PGF$_1$, amide;
(4Z)-9-deoxy-5,9$\alpha$-epoxy-$\Delta$4-trans-$\Delta$2-13,14-dihydro-PGF$_1$, amide;
(4Z)-9-deoxy-5,9$\alpha$-epoxy-$\Delta$4-trans-$\Delta$2-17-phenyl-18,19,20-t rinor-PGF$_1$, amide;
(4Z)-9-deoxy-5,9$\alpha$-epoxy-$\Delta$4-trans-$\Delta$2-16-phenoxy-17,18,19,20-tetranor-PGF$_1$, amide;
(4Z)-9-deoxy-5,9$\alpha$-epoxy-$\Delta$4-trans-$\Delta$2-16-(m-chlorophenoxy)-17,18,19,20-tetranor-PGF$_1$, amide;
(4Z)-9-deoxy-5,9$\alpha$-epoxy-$\Delta$4-trans-$\Delta$2-16-($\alpha,\alpha,\alpha$-trifluoro-p-tolyloxy)-17,18,19,20-tetranor-PGF$_1$, amide;
(4Z)-9-deoxy-5,9$\alpha$-epoxy-$\Delta$4-trans-$\Delta$2-13,14-dihydro-16-phenoxy-17,18,19,20-tetranor-PGF$_1$, amide; and
(4E)-9-deoxy-5,9$\alpha$-epoxy-$\Delta$4-trans-$\Delta$2-PGF$_1$, amide.

I claim:
1. A 4Z compound of the formula

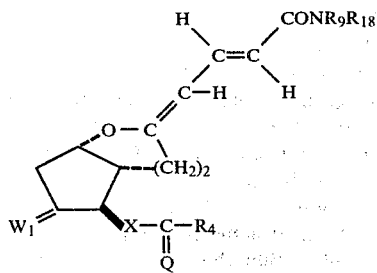

wherein $W_1$ is $\alpha$—OH:$\beta$—H, $\alpha$—H:$\beta$—OH, oxo, methylene, $\alpha$—H:$\beta$—H, $\alpha$—CH$_2$OH:$\beta$—H;
wherein Q is oxo, $\alpha$-H:$\beta$-H; $\alpha$-OH:$\beta$-$R_8$ or $\alpha$—$R_8$:$\beta$—OH
wherein $R_8$ is hydrogen or alkyl of one to 4 carbon atoms, inclusive; and
wherein $R_4$ is
(1) —CR$_5$R$_6$—C$_g$H$_{2g}$—CH$_3$ or
(2) —CR$_5$R$_6$—Z—(Ph)
wherein C$_g$H$_{2g}$ is alkylene of one to 9 carbon atoms, inclusive, with one to 5 carbon atoms, inclusive, in the chain between —CR$_5$R$_6$— and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa (—O—); wherein Z represents an oxa atom (—O—) or C$_j$H$_{2j}$ wherein C$_j$H$_{2j}$ is a valence bond or alkylene of one to 9 carbon atoms, inclusive, with one to 6 carbon atoms, inclusive between CR$_5$R$_6$— and the (Ph); wherein (Ph) is phenyl or phenyl substituted by one, 2, or 3 alkyl of one to 4 carbon atoms, inclusive, fluoro, chloro, trifluoromethyl, or —OR$_7$, wherein $R_7$ is alkyl of one to 4 carbon atoms, inclusive, with the proviso that not more than two such substituents are other than alkyl, such substituents being either the same or different;
wherein $R_9$ is hydrogen, methyl, or ethyl, and wherein $R_{18}$ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive; and
wherein X is
(1) trans—CH=CH—,
(2) cis—CH=CH—,
(3) —C≡C—, or
(4) —CH$_2$CH$_2$—;
including the lower alkanoates thereof.

2. A compound according to claim 1, wherein Q is $\alpha$—OH:$\beta$—$R_8$ or $\alpha$—$R_8$:$\beta$—OH, and $W_1$ is $\alpha$—OH:$\beta$—H, $\alpha$—H:$\beta$—OH, or $\alpha$—H:$\beta$—H.

3. A compound according to claim 2, wherein $W_1$ is $\alpha$—OH:$\beta$—H.

4. A compound according to claim 3, wherein $\alpha$ is $\alpha$—OH:$\beta$—$R_8$.

5. A compound according to claim 4, wherein $R_4$ is —CR$_5$R$_6$—C$_g$H$_{2g}$—CH$_3$.

6. A compound according to claim 4, wherein $R_4$ is —CR$_5$R$_6$(Ph).

7. A 4E compound of the formula

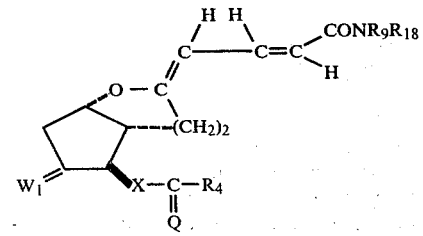

wherein $W_1$ is $\alpha$—OH:$\beta$—H, $\alpha$—H:$\beta$—OH, oxo, methylene, $\alpha$—H:$\beta$—H, $\alpha$—CH$_2$OH:$\beta$—H;
wherein Q is oxo, $\alpha$—H:$\beta$—H, $\alpha$—OH:$\beta$—$R_8$ or $\alpha$—$R_8$:$\beta$—OH wherein $R_8$ is hydrogen or alkyl of one to 4 carbon atoms, inclusive; and wherein $R_4$ is
(1) $-CR_5R_6-C_gH_{2g}-CH_3$ or
(2) $-CR_5R_6-Z-(Ph)$ wherein $C_gH_{2g}$ is alkylene of one to 9 carbon atoms, inclusive, with one to 5 carbon atoms, in the chain between $-CR_5R_6-$ and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between $CR_5R_6-$ and the (Ph); wherein (Ph) is phenyl or phenyl substituted by one, 2, or 3 alkyl of one to 4 carbon atoms, inclusive, fluoro, chloro, trifluoromethyl, or $-OR_7$, wherein $R_7$ is alkyl of one to 4 carbon atoms, inclusive, with the proviso that not more than two such substituents are other than alkyl such substituents being either the same or different;

wherein $R_9$ is hydrogen, methyl, or ethyl, and wherein $R_{18}$ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive; and wherein X is
(1) trans—CH=CH—,
(2) cis—CH=CH—,
(3) —C≡C—, or
(4) —CH$_2$CH$_2$—;

including the lower alkanoates thereof.

8. A compound according to claim 7, wherein Q is $\alpha$—OH:$\beta$—R$_8$, wherein W$_1$ is $\beta$—OH:$\beta$—H, and wherein R$_4$ is —CR$_5$R$_6$—C$_g$H$_{2g}$—CH$_3$.

* * * * *

UNITED STATES PATENT OFFICE
CERTIFICATE OF CORRECTION

Patent No. 4,235,783   Dated 25 November 1980

Inventor(s) Roy A. Johnson

It is certified that error appears in the above-identified patent and that said Letters Patent are hereby corrected as shown below:

The title should read -- Trans-2,3,4,5-Tetradehydro-9-Deoxy-5,9α-Epoxy-PGF$_1$ Amides --;

Column 1, line 55, and Column 4, line 8, "-CR$_5$R$_6$-C$_g$H$_{2g}$=CH$_3$" should read -- -CR$_5$R$_6$-C$_g$H$_{2g}$-CH$_3$ --;

Column 6, line 18, "W$_1$ is β-OH:β-H," should read -- W$_1$ is α-OH:β-H, --.

Signed and Sealed this

Seventh Day of April 1981

[SEAL]

Attest:

RENE D. TEGTMEYER

Attesting Officer   Acting Commissioner of Patents and Trademarks